United States Patent [19]

Patton

[11] 3,948,941

[45] Apr. 6, 1976

[54] PREPARATION OF IMIDES USING CN⁻ CATALYSTS

[75] Inventor: Tad L. Patton, Baytown, Tex.

[73] Assignee: Exxon Research and Engineering Company, Linden, N.J.

[22] Filed: Oct. 26, 1973

[21] Appl. No.: 410,210

[52] U.S. Cl. 260/326 N; 260/326 S; 260/326.5 FM; 260/78 TF
[51] Int. Cl.² .............. C07D 209/48; C07D 207/40
[58] Field of Search .. 260/326.N, 326 R, 326.5 FM, 260/78 TF

[56]  References Cited
UNITED STATES PATENTS

| | | | |
|---|---|---|---|
| 3,300,420 | 1/1967 | Frey | 260/78 TF |
| 3,314,923 | 4/1967 | Muller et al. | 260/326 N |
| 3,445,477 | 5/1969 | Muller et al. | 260/326 N |
| 3,493,540 | 2/1970 | Muller et al. | 260/30.8 R |
| 3,701,756 | 10/1972 | Carleton et al. | 260/326 R |

OTHER PUBLICATIONS

Hilt et al., "Chem. Abstracts", Vol. 66, p. 8990, No. 95724P, (1967).

*Primary Examiner*—Lewis Gotts
*Assistant Examiner*—S. P. Williams
*Attorney, Agent, or Firm*—David A. Roth

[57]  ABSTRACT

An improved process for preparing imides comprises reacting acid anhydrides with organic isocyanate groups in the presence of cyanide ion as a catalyst.

20 Claims, No Drawings

PREPARATION OF IMIDES USING CN⁻ CATALYSTS

CROSS-REFERENCE TO RELATED APPLICATIONS

This application is not related to any other applications owned by the same assignee except for a copending, commonly assigned application filed on the same day which also covers the use of cyanide ion as a catalyst in a particular polymerization reaction.

PRIOR ART

Imides are well known in the art. Polyimides, for instance, are usually prepared by either of two reactions. A dianhydride is reacted with a diamine, or alternately, a dianhydride is reacted with a diisocyanate. In the first reaction an intermediate polyamic acid is first formed and it is cyclized to a polyimide by a subsequent heating reaction.

Also, low molecular weight imides are made by similar type reactions. A typically useful material is N, N'-diphenylmethanebismaleimide having the following formula:

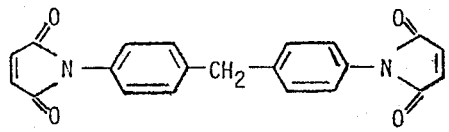

N, N'-m-phenylenebismaleimide, N, N'-methyl-2,4-phenylenebismaleimide are useful, particularly for cross-linking reactions and as dienophiles in polymerization reaction and Diels-Alder type reactions.

These materials, because of their di-olefinic structures are used as cross-linking agents. They also can be made to polymerize with diamines and disulfides by an addition type reaction across the double bond.

It would be useful and economically advantageous if improved synthetic methods were available to produce imides of the above description as well as other species in the broad class of imides.

SUMMARY OF THE INVENTION

The invention comprises an improved process for preparing imides from isocyanates and acid anhydrides by using a catalytic quality of cyanide ion, i.e. CN⁻.

DESCRIPTION OF THE INVENTION WITH PREFERRED EMBODIMENTS

It has been found and forms the basic feature of this invention that the reaction between an isocyanate group and an acid anhydride to form an imide can be greatly improved and made more efficient by utilizing a cyanide ion as an appropriate catalyst.

The cyanide ion is generally obtained from a solution of a cyanide salt and is preferably a metal cyanide salt or a quaternary ammonium cyanide, e.g. (Et₃ NH⁺ CN⁻). Typical salts from which the cyanide ion may be obtained include NaCN, KCN, Zn(CN)₂ and Cd(CN)₂; preferable salts are NaCN and KCN.

The particular salt or other compound from which the cyanide ion is derived is not critical. The cyanide salts should be soluble in the solvent to be used in the particular system. Dipolar aprotic solvents are used as reaction media for many of the reactions in which imides are formed, especially when those reactions are designed to result in polyimides.

Sodium cyanide is very soluble in hexamethylphosphormamide, dimethylsulfoxide, dimethylformamide, dimethylacetamide, and N-methylpyrollidone. Dimethylsulfoxide and hexamethylphosphormamide are good solvents for KCN.

In the event that solvents are to be used in which the particular cyanide salt is not particularly soluble, the problem can be ameliorated by dissolving the cyanide in a solvent in which it is particularly soluble and which will dissolve in the reaction medium. Then this particular concentrate of cyanide ion is mixed in with the reactant solution.

the cyanide ion is present in catalytic amounts sufficient to accomplish its purpose. An excess of catalytic agent can always be present, but it is clear that utilizing an excess of catalyst beyond that quantity necessary to promote the reaction as desired, is simply a waste of catalyst, and could be quite uneconomical, as well as presenting a problem of separating the catalyst salt from the resulting products.

Very generally, a suitable amount of cyanide ion to use in the reaction will be about $10^{-4}$ to $10^{-1}$ moles/l., preferably $10^{-3}$ to $10^{-2}$ moles/liter.

Cyanide ion is a very effective catalyst for the herein described reaction. It is postulated that the cyanide ion may act by attacking an anhydride group to form a cyanoformyl carboxylate anion

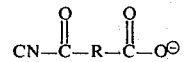

This intermediate could then attack an isocyanate group to form the intermediate anion below which cyclizes and loses carbon dioxide to form an imide; the cyanide ion is liberated and becomes available for additional reaction.

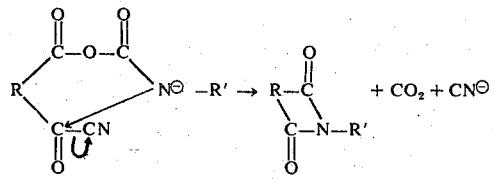

An alternate hypothesis is that the cyanide ion also catalyzes the reaction by first adding to an isocyanate group to form a cyanoformamidyl anion

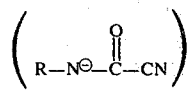

which then attacks an anhydride group to form an imide group as follows:

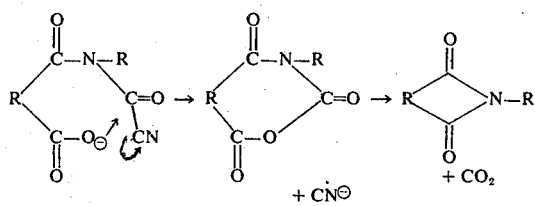

In its most elementary aspect, the invention is schematically illustrated by the formulae which follows:

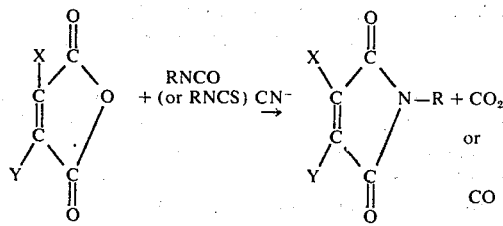

wherein:
X represents hydrogen or a $C_2$ to $C_{20}$ optionally substituted alkyl, arylalkyl, or aryl radical or diaryl radical, and

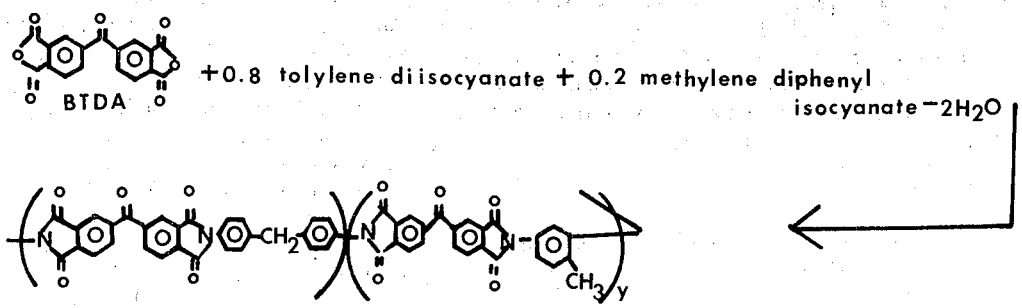

Y has the same meaning as X,
and X and Y together can represent a $C_4$ to $C_{40}$ portion of an aromatic or substituted aromatic ring structure, and one substituted with another anhydride group; and
wherein:
R is a $C_4$ to $C_{60}$ hydrocarbon or substituted hydrocarbon substituent, i.e. aliphatic, aromatic or a combination thereof especially a substituent with at least one other NCO (or NCS) group.

Thus in its most basic aspects the invention is used to promote the reaction of one NCO group with one anhydride group. Variations of this reaction are logical. The reaction can be used with a dianhydride and a mono NCO or conversely when a di or poly NCO is reacted with a mono anhydride group to make novel functionally substituted imides. Further, compounds containing two or more NCO groups can be reacted with compounds containing two or more anhydride groups, e.g. dianhydrides, trianhydrides, etc., to form polymers which contain imide structures.

Typical examples of the type of reaction in which the catalyst of the invention is extremely useful include such things as the preparation of alkyl or aryl bismaleimides such as m-phenylene, bismaleimide, 4-methyl-m-phenylene bismaleimide, methylene diphenyl bismaleimide and other maleimides of the general formula as follows:

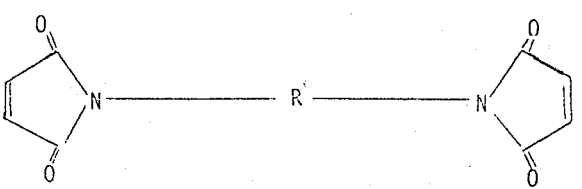

wherein R is the same as described above.

The cyanide ion catalyst finds special utility when it is used to make polyimides or polymers which contain imide groups. A general polyimide process in which the catalyst of the invention is particularly applicable and preferred is as follows:

Diisocyanates are reacted with tetracarboxylic dianhydrides in an appropriate solvent. German patent application No. 2,143,080 discloses this process of making polyimides without the instant catalyst in which benzophenone tetracarboxylic dianhydride is reacted with mixtures of toluene diisocyanate and diphenyl methane diisocyanate. The same reaction can also be used to make foamed products as set forth in U.S. Pat. No. 3,562,189, British Pat. No. 1,272,201, and U.S. Pat. No. 3,620,987. The reaction is schematically illustrated as follows:

Generally, in the most favorable anhydride situations ring formation will take place when the carboxyl groups of the dicarboxylic acid are separated by no more than two or three carbon atoms. Maleic anhydrides and succinic anhydrides are simple examples of such anhydrides, the difference being that one is saturated and the other is not.

Anhydrides useable in the invention are derived, for example from pyromellitic acid; trimellitic acid; mellitic acid naphthalene-1,4,5,8-, naphthalene-2,3,6,7- or naphthalene-1,2,5,6- tetracarboxylic acid; from diphenyl ether-3,3', 4,4', or diphenyl-3,3', 4,4'- or diphenyl ether-2,2', 3,3'- or diphenyl-2,2', 3,3'- tetracarboxylic acids; from 2,2-bis-(3,4-dicarboxyphenyl)-propane; from bis-(3,4-dicarboxyphenyl)-sulphone; from perylene-3,4,9,10-tetracarboxylic acid or from ethylene tetracarboxylic acid, also succinic anhydride, maleic anhydride, phthalic anhydride, substituted phthalic anhydrides.

The anhydrides of hydroxy-, mercapto- or amino-substituted o-phthalic acids; and of hydroxy-, mercapto- or amino-substituted naphthalene dicarboxylic acids whose carboxyl groups are on adjacent carbon atoms of the naphthalene ring, can also be used. Bis-adducts of maleic acid or maleic anhydride with styrene or substituted styrenes are also suitable for the purposes of the process according to the invention, as are phenylene-bis-alkane-di-(carboxylic acid anhydrides), of the kind described in Belgian patent specification No. 613,374, bicyclotetracarboxylic acid dianhydrides of the kind described in U.S. Pat. No. 3,037,966, and as are polyanhydrides obtained by chlorinating paraffins in the presence of, for example, maleic acid anhydride.

Also included are anhydrides which are formed by a Diels-Alder type reaction of maleic anhydride with conjugated dienes and substituted conjugated dienes such as cyclopentadiene, hexachlorocyclopentadiene, butadiene, conjugated diene butyl, etc.

The compounds used as anhydride components may also be of a more or less polymeric nature, for example bis-trimellitic anhydride esters of the structural formula

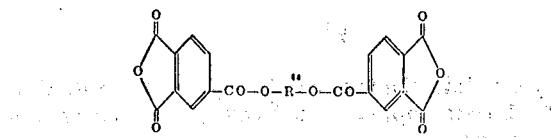

may also be used here. In this structural formula, R'' represents a saturated or an unsaturated, aliphatic or cycloaliphatic bivalent radical in which aromatic, cycloaliphatic or heterocyclic ring systems and ether-, ester-, sulphide, sulphoxide- or sulphone bridges may be incorporated, and which may optionally be substituted by chlorine, bromine or iodine atoms or by a nitro-, alkoxy- or mercapto group.

The following are examples of R'':

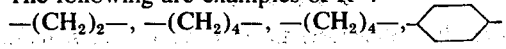

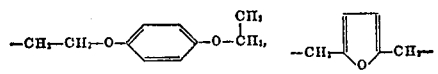

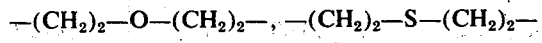

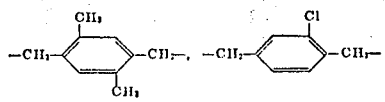

—CH$_2$—CH=CH—CH$_2$—, —CH$_2$—C ≡ C—CH$_2$—

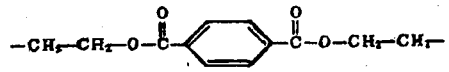

The monoisocyanates, diisocyanates or polyiscyanates used in the invention are selected from a broad group having a large variety of organic moieties. The organic moieties of these isocyanates can be substituted with groups such as alkyl, aryl, halogens, sulfoxy, sulfonyl, alkoxy, aryloxy, oxo, ester, alkylthio, arylthio, nitro and the like which do not react with the isocyanate or anhydride group. Functional groups which have active hydrogen atoms (e.g. carboxylic acids, hydroxyl groups, amines, etc.) should not be present.

Each isocyanate may be characterized by its specific organic moiety. For example, those diisocyanates having an aliphatic hydrocarbon moiety are exemplified by tetramethylene diisocyanate; hexamethylene diisocyanate; dodecamethylene diisocyanate; 2,2,4-trimethylhexamethylene diisocyanate; and the like. Diisocyanates characterized by having aromatic hydrocarbon moieties are exemplified by m-phenylene diisocyanate; p-phenylene diisocyanate; biphenylene diisocyanate; 1,5-naphthalene diisocyanate; and the like. A diisocyanate having an alicyclic hydrocarbon moiety is 1,4-diisocyanato cyclohexane and 3-isocyanato-methyl-3,5,5-trimethylcyclohexyl isocyanate.

The diisocyanates containing more than one type of hydrocarbon moiety are exemplified by toluene diisocyanate; durene diisocyanate; 4, 4'-diphenylmethane diisocyanate; 3,3'dimethyl-4,4'-diphenylene diisocyanate; 4,4'-diphenylisopropylidene diisocyanate; p-xylylene diisocyanate; m-xylylene diisocyanate; 4,4'-methylene bis(cyclohexyl isocyanate); 4=(4-isocyanatocyclohexyl) phenylisocyanate; 4-isocyanatobenzyl isocyanate; and the like.

It is noted that in the foregoing examples the isocyanate groups in each of the diisocyanates may be attached to the same or different hydrocarbon portions of the organic moiety.

Further, diisocyanates which have organic moieties containing functional groups may also be used and are exemplified by 4,4'-diphenylsulfone diisocyanate; 4,4'-diphenylether diisocyanate; 3,3'-dimethoxy-4,4'-diphenylene diisocyanate; di(3-isocyanato-propyl)ether; tetrafluoro-p-phenylene diisocyanate; tetrafluoro-m-phenylene diisocyanate; 4,4'-diisocyanate-octafluorobiphenyl and the like. Mixtures of the diisocyanates may be used.

Diisocyanate, as used herein, is a general class of compounds meant to include those compounds which have polymeric organic moieties such as the prepolymer diisocyanates which are used in the field of urethane polyers. Further, specific diisocyanates which may be used in the present invention are found in patents, articles, or organic textbooks; a specific example being the paper "Mono and Polyisocyanates" by W. Sieflken, Annalen der Chemie, 562, 6–136 (1949), which is incorporated herein by reference.

Examples of suitable monoisocyanates are phenylisocyanate, or substituted phenyl isocyanates such as chloro, bromo, nitro, and alkoxy phenyl isocyanates, n-butyl isocyanate, octyl isocyanate, and allyl isocyanate. In general, aromatic isocyanates are more reactive than aliphatic isocyanates and therefore are usually preferred.

Any suitable solvent can be used in the reaction of the invention. Indeed mixtures of solvents can be utilized in which the resulting solution is such that the reactants themselves are soluble but the resulting products are insoluble. Thus the product precipitates out as it forms and is easy to separate from the solvent and starting materials.

Very generally, the preferred solvents are dipolar aprotic solvents.

These are defined as molecules with a substantial dipole moment arising from a charge separation within a group of two or three atoms. Aprotic molecules do not have a hydrogen cabable of ionization or hydrogen bonding. Dipolar aprotic solvents solvate cations strongly. The negative end of the solvent dipole is the one which is strongly associated with the cations from the cyanide salt.

Therefore, anions such as CN are liberated from the influence of the cation and are therefore readily available to interact with polar groups such as NCO and anhydride groups. The descreased solvation of these anions in such solvents enhances their reactivity in ionic or ionically catalyzed reactions.

Generally speaking, typical aprotic dipolar solvents useful in this reaction are:

Dimethylsulfoxide
Tetrahydrothiophene dioxide (sulfolane)
Pyridine-1-oxide
Nitrobenzene Acetonitrile
Benzonitrile
Dimethylformamide
Dimethylacetamide
1-Methyl-2-pyrrolidone
Acetone
Trimethylphosphine oxide
Hexamethylphosphoramide The invention will be more clearly understood by reference to the following examples wherein parts and percentages are by weight unless otherwise indicated. These examples illustrate specific embodiments of the present invention and should not be construed to limit the invention in any way.

EXAMPLE 1

In this example, benzophenone tetracarboxylic dianhydride (BTDA) was reacted with diphenyl methane diisocyanate (MDI), illustrated schematically as follows, under conditions with a cyanide ion catalyst and without a cyanide ion catalyst.

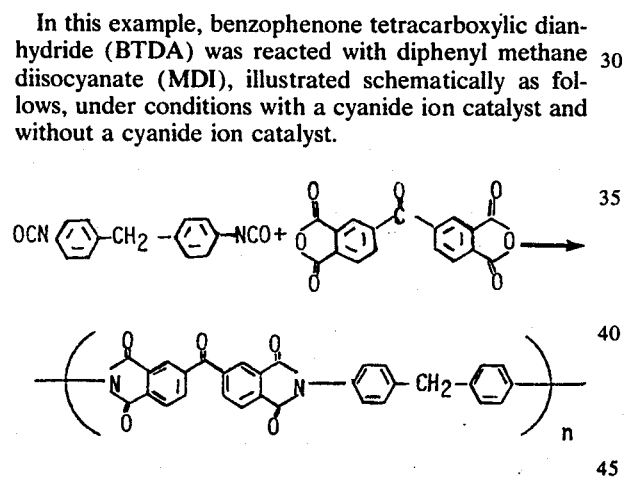

| Materials | Cyanide Ion | No Cyanide Ion |
|---|---|---|
| BTDA | 9.6 g | 9.6 g. |
| MDI | 7.5 g. | 7.5 g. |
| DMF (dry) | 75 ml. | 75 ml. |
| NaCN | 0.0147 g. | None |

| Time | Procedure Operation | Observations | |
|---|---|---|---|
| 0 | Add MDI in 25 ml. of DMF to BTDA in 50 ml. of DMF | 22° C. | 22° C. |
| 6 min. | Addition complete | 22° C. | 22° C. |
| 10 min. | | dark solution | yellow solution |
| 21 min. | | Solids beginning to separate | clear solution |
| 65 hrs. | | Thick suspension of sandy granular solids | clear gels* |

*Cross-linked

The above reactions occurred in the absence of heat.
The products have not been rigorously analyzed yet but it appears that the product formed in the presence of CN⁻ was similar to a polyamide type product.

EXAMPLE 2

This example illustrates the reaction of the following compounds:

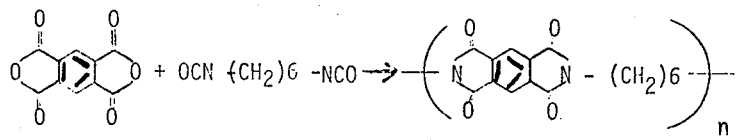

Pyromellitic dianhydride (10.9 g.) was dissolved in 175 ml. DMF saturated with NaCN (1.61 × 10⁻⁴ moles CN⁻ per ml.).

Then 8.4 g. of hexamethylene diisocyanate was added. Within two minutes $CO_2$ began to be evolved.

After 11 minutes the gas evolution was very rapid, and the temperature had increased from 30° to 36°C. After 75 minutes the solution was poured into acetone to precipitate a hard granular product.

This product was washed with acetone and dried at 140°C.

EXAMPLE 3

This example illustrates the invention in the reaction of the following compounds:

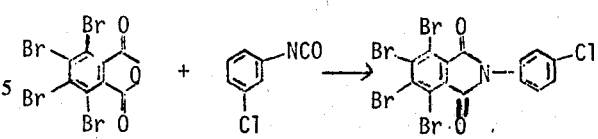

Tetrabromophthalic anhydride (46.3 g.) and m-chlorophenyl isocyanate (15.4 g.) were dissolved in 250 ml. DMF. Then 20 ml. of DMF saturated with sodium cyanide (3.22 × 10⁻³ moles CN⁻) was added.

Carbon dioxide was liberated very slowly. After an hour it was heated to 80° C. Carbon dioxide continued to be evolved for three hours then ceased. The solution was poured into water to precipitate a yellow powder.

The resulting product appears to be a novel composition of matter. It also appears to have excellent utility as a flame retardant for polyparabanic acid type polymer. It will probably be a suitable flame retardant for polyimides and similar heterocyclic polymers.

EXAMPLE 4

A polyimide was prepared by the technique of the invention according to the following reaction:

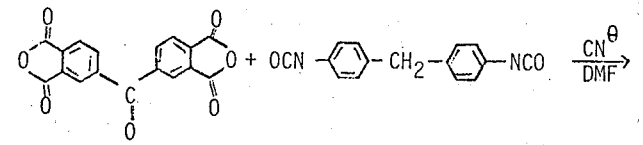

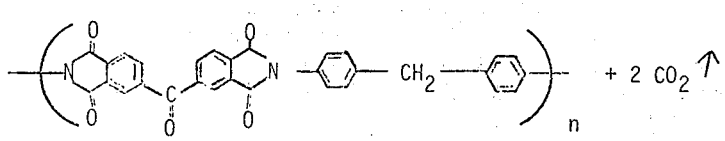

Reagents:
BTDA (benzophenone tetracarboxylic dianhydride), 16.6 g. (0.05 mole)
MDI 12.5 g. (0.05 moles)
DMF 200 ml. (redistilled)
DMF saturated with NaCN ($1.61 \times 10^{-4}$ moles $CN^{\ominus}$ per ml.), 30 ml.

Procedure:
A 3-necked flask (500 ml.) was flushed with nitrogen.
Then the dianhydride and DMF were introduced after solution was complete, the diisocyanate (MDI) was added. Reaction observations are itemized below:

| Time (Min.) | °C. | Operation and Observations |
|---|---|---|
| 0 | 25 | BTDA, MDI, and DMF all in solution. The solution is yellow. |
| 5 | 25 | No $CO_2\nearrow$. Add 70 ml. of NaCN solution |
| 6 | 26 | $CO_2$ liberated, pink-orange colored solution. |
| 8 | 27.5 | Add heat. Yellow solution. |
| 16 | 45 | Add 10 ml. NaCN Solution. |
| 18 | 47 | $CO_2\nearrow$ |
| 20 | 54 | $CO_2$ liberation, about 120 bubbles per minute. |
| 23 | 62 | Yellow precipitate forming. Much $CO_2\nearrow$. |
| 45 | 68 | $CO_2\nearrow$ slowing. Add 10 ml. NaCN solution. No additional $CO_2$ rate |
| 62 | 68 | Remove heat (no more $CO_2$ liberated). Flush with nitrogen. |

An attempt to filter the yellow powder plugged the filter. The product was separated from the solvent by tube centrifugation. The solvent was decanted off and the powder washed with benzene and recentrifuged. The effluent was decanted off.

The yellow powder was resuspended in hexane and then filtered on a coarse, fritted glass funnel. It was dried in vacuo at 120° C. in a nitrogen purge. Yield = 24 grams of bright yellow powder. M. P. 300° C. TGA — no precipitous weight loss below 500° C.

EXAMPLE 5

A polyimide was prepared by the technique of the invention according to the following indicated reaction.

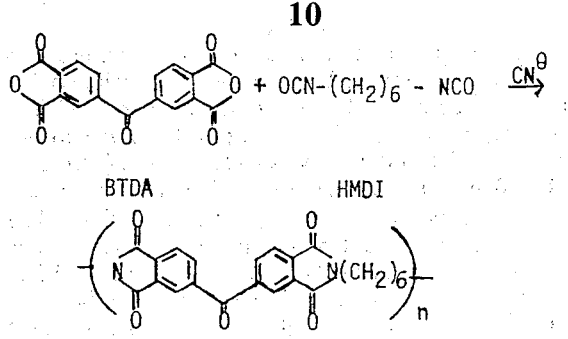

Reagents:
BTDA, 16.6 g. (0.05 mole)
HMDI 8.40 g. (0.05 mole)
DMF, 150 ml.

DMF saturated with NaCN, 30 mil.
Procedure:
The BTDA was dissolved in the DMF using the apparatus described in Example 4. Then the HMDI was added. Raction observatins appear below.

| Time (Min.) | °C. | Operations and Observations |
|---|---|---|
| 0 | 35 | HMDI added. Heat added. |
| 14 | 55 | No $CO_2$. |
| 15 | 57 | Add 10 ml. NaCN Solution. |
| 19 | 61 | First $CO_2$ (slow). |
| 20 | 70 | $CO_2$ bubbles, 1/15 sec. |
| 38 | 87 | Add 10 ml. catalyst solution. |
| 40 | 89 | 16 bubbles $CO_2$ per min. |
| 49 | 96 | 34 bubbles $CO_2$ per min. |
| 62 | 105 | 52 bubbles $CO_2$ per min. |
| 100 | 103 | 20 bubbles $CO_2$ per min. |
| 103 | 103 | Add 10 ml. NaCN solution. |
| 110 | 100 | 20 bubbles $CO_2$ per min. |
| 120 | 102 | 43 bubbles $CO_2$ per min. |
| 155 | 105 | 1–2 bubbles $CO_2$ per min. (slow!) |

Heat was removed and the reaction mixture was purged with nitrogen. Upon cooling the solution became opaque at 30° C. The solution was poured into water to precipitate a fine white powder which coagulated when HCl (10 ml.) was added. It was filtered.

The fine white powder was washed with methanol. When benzene was put in it, it became sticky. The sticky material was put in methanol to solidify it. It was filtered and dried at 120° C./vac. oven. Yield = 16.2 g. It softened at 245° C. on a Fisher Johns m.p. block.

The polymer exhibited adhesive properties in that it melt stuck two pieces of glass together and it did not crystallize.

EXAMPLE 6

The following reaction using cyanide ion as catalyst was carried out:

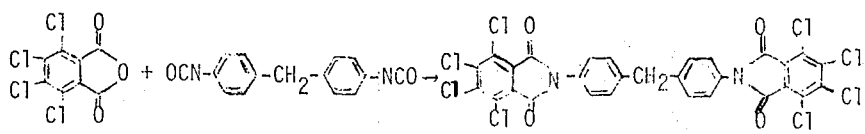

Reagents:
MDI, 12.5 g. (0.05 mole)
Tetrachlorophthalic anhydride, 31.5 g. (0.21 mole)
DMF, 250 ml. + 50 ml. = 300 ml.
DMF saturated with NaCN (1.61 × $10^{-4}$ mold $CN^{\ominus}$/ml.), 31.2 mole.

Procedure:
The anhydride was dissolved in 200 ml. DMF. Then the MDI was added, followed by 50 ml. DMF. The clear solution was in a 500 ml., three-necked flask fitted with a condenser thermometer, and gas purge needle for $N_2$ purge. The top of the condensor was connected to a trap and bubbler filled with clear $Ba(OH)_2$ solution to detect $CO_2$.

The $N_2$ purge was stopped. The catalyst solution (NaCN in DMF) was added. Gas evolved immediately and steadily (about 1 bubble/2 sec.). The almost colorless solution become a dark yellow (almost orange). The reaction observations were as follows:

| Time (Min.) | ° C. | Operation and Observation |
|---|---|---|
| 0 | 24 | Add catalyst solution |
| 1 | 26 | $CO_2$ evolving; solution yellow-orange |
| 2 | 27 | |
| 5 | 28 | |
| 10 | 29 | Light yellow color |
| 24 | 29 | |
| 41 | 29 | Purge and slow $N_2$ stream during |
| 45 | 28.5 | Cooling by $N_2$ |
| 48 | 28.5 | |
| 120 | 27.0 | Stop $N_2$ purge $CO_2$ still evolved. |
| 175 | 26.0 | |
| 212 | 26 | Light yellow color. Add heat. |
| 228 | 37 | |
| 250 | 53 | |
| 272 | 63 | Remove heat; cool to 40° C. |

A clear solution was poured into ice and water to precipitate a finely divided pale yellow solid. Yield = 24 g. m.p. 357° C.

EXAMPLE 7

The preceding Example 6 was repeated except without using sodium cyanide.
Reagents:
MDI, 12.5 g. (0.05 mole)
Tetrachlorophthalic anhydride, 31.5 g. (0.11 mole)
DMF, 300 ml.

Procedure:
The anhydride was dissolved in the DMF, then the MDI was added. The yellow solution gave off very little $CO_2$. The reaction observations were as follows:

| Time(Min.) | ° C. | Operations and Observations |
|---|---|---|
| 0 | 25 | Add MDI to anhydride solution |
| 5 | 25 | Solution clear |
| 12 | 25 | Very slow evolution of $CO_2$. |
| 16 | 26 | |
| 29 | 27 | One $CO_2$ bubble every 15–30 seconds |
| 54 | 27 | |
| 72 | 27 | |
| 130 | 27 | No more $CO_2$ evolution. |
| 166 | 26.5 | No $CO_2$. |

The reaction solution was discarded. Most of the MDI was unreacted since on contact with water it was rapidly hydrolyzed and gave off $CO_2$.

Conclusion:
Very little reaction occurs between MDI and tetrachlorophthalic anhydride in the absence of cyanide ion (or other suitable catalyst).

What is claimed is:

1. In the process of preparing imides by the reaction of carboxylic anhydrides with organic isocyanates, the improvement which comprises:
utilizing a $CN^-$ ion as the catalyst.

2. A method according to claim 1 wherein said catalyst is derived from sodium cyanide.

3. A method according to claim 1 wherein said anhydride is a dianhydride.

4. A method according to claim 1 wherein said anhydride is a mono anhydride.

5. A method according to claim 1 wherein said isocyanate is a diisocyanate.

6. A method according to claim 1 wherein said isocyanate is a monoisocyanate.

7. A method according to claim 1 wherein said isocyanate is a diisocyanate and said anhydride is a dianhydride.

8. A method according to claim 1 wherein said anhydride is a trianhydride.

9. A method according to claim 1 wherein said isocyanate is a polyisocyanate containing from 2 to 6 isocyanate groups.

10. A method according to claim 1 wherein said anhydride is maleic anhydride.

11. A method according to claim 1 wherein said isocyanate is a diisocyanate and each isocyanate group reacts with one maleic anhydride group to result in the formation of bis-maleimides.

12. A method according to claim 1 wherein said anhydride is a benzophenone tetracarboxylic acid dianhydride and said isocyanate is selected from the group consisting of toluene diisocyanate, a diphenyl methane diisocyanate or a combination of the two.

13. A method according to claim 1 wherein said anhydride is a pyromellitic dianhydride and said isocyanate is selected from the group consisting of toluene diisocyanate diphenyl methane diisocyanate or a combination of the two.

14. A method according to claim 5 wherein said isocyanate is a diphenyl ether diisocyanate.

15. A method according to claim 4 wherein said anhydride is tetrabromophthalic anhydride.

16. A method according to claim 6 wherein said anhydride is tetrabromophthalic anhydride and the said isocyanate is chlorophenyl isocyanate.

17. A method according to claim 4 wherein the said anhydride is tetrachlorophthalic anhydride.

18. A method according to claim 5 wherein said anhydride is tetrachloro phthalic anhydride and the diisocyanate is diphenylmethane diisocyanate.

19. A method according to claim 7 wherein the diisocyanate is hexamethylene diisocyanate and the dianhydride is pyromellitic dianhydride.

20. A method according to claim 7 wherein the diisocyanate is hexamethylene diisocyanate and the dianhydride is benzophenonetetracarboxylic dianhydride.

* * * * *